(12) United States Patent
Watts et al.

(10) Patent No.: US 6,200,602 B1
(45) Date of Patent: Mar. 13, 2001

(54) COMPOSITION FOR ENHANCED UPTAKE OF POLAR DRUGS FROM THE COLON

(75) Inventors: Peter James Watts; Lisbeth Illum, both of Nottingham (GB)

(73) Assignee: West Pharmaceutical Services Drug Delivery & Clinical Research Centre Limited, Nottingham (GB)

( * ) Notice: Subject to any disclaimer, the term of this patent is extended or adjusted under 35 U.S.C. 154(b) by 0 days.

(21) Appl. No.: 09/011,306

(22) PCT Filed: Aug. 8, 1996

(86) PCT No.: PCT/GB96/01933

§ 371 Date: Mar. 30, 1998

§ 102(e) Date: Mar. 30, 1998

(87) PCT Pub. No.: WO97/05903

PCT Pub. Date: Feb. 20, 1997

(30) Foreign Application Priority Data

Aug. 8, 1995 (GB) .................................. 9516268

(51) Int. Cl.$^7$ .............................. A61K 9/28; A61K 9/62

(52) U.S. Cl. .................... 424/463; 424/451; 424/452; 424/457; 424/458; 424/459; 424/461; 424/464; 424/474; 424/475; 424/479; 424/480; 424/489; 424/490; 424/496

(58) Field of Search .................... 424/451, 452, 424/457, 458, 459, 461, 463, 464, 474, 475, 479, 480, 489, 490, 494

(56) References Cited

U.S. PATENT DOCUMENTS 4,871,549  10/1989  Ueda et al.

FOREIGN PATENT DOCUMENTS

| 195 40 669 A1 | 5/1996 | (DE) . |
| 0 332 222 B1 | 9/1989 | (EP) . |
| 0 351 651 B1 | 1/1990 | (EP) . |
| 0 418 674 A1 | 3/1991 | (EP) . |
| 2 238 243 | 5/1991 | (GB) . |
| WO 89/11269 A1 | 11/1989 | (WO) . |
| WO 91/11175 A1 | 8/1991 | (WO) . |
| WO 91/16881 A1 | 11/1991 | (WO) . |
| WO 94/08622 A1 | 4/1994 | (WO) . |
| WO 95/14037 A1 | 5/1995 | (WO) . |

OTHER PUBLICATIONS

Ashford, et al., "In Vivo Assessment of Colonic Drug Delivery Systems," *Br. Pharm. Conference* Abstract 13, p. 1049 (1992).

(List continued on next page.)

*Primary Examiner*—Gollamudi S. Kishore
(74) *Attorney, Agent, or Firm*—Arnall Golden & Gregory, LLP (57) ABSTRACT

The invention provides a drug delivery composition for colonic delivery comprising a polar drug, an absorption promoter which (a) comprises a mixture of a fatty acid having 6 to 16 carbon atoms or a salt thereof and a dispersing agent, or (b) comprises a mixture of mono/diglycerides of medium chain fatty acids and a dispersing agent, and means adapted to release the polar drug and absorption promoter in the colon following oral administration. A preferred fatty acid is capric acid or a salt thereof. Colon specific delivery can be achieved by providing the composition in a capsule, tablet or pellet which is coated with a material which dissolves in the small intestine or is degraded by the conditions in the colon.

16 Claims, 11 Drawing Sheets

OTHER PUBLICATIONS

Beskid, et al., "Enteral, Oral and Rectal Absorption of Ceftriaxone Using Glyceride Enhancers," *Chemotherapy* 34:77–84 (1988).

Davis, "Delivery Systems for Biopharmaceuticals," *J. Pharm. Pharmacol.* 44(Supp. 1):186–90 (1992).

Kajii, et al., "Fluorescence Study of the Membrane–Perturbing Action of Sodium Caprylate as Related to Promotion of Drug Absorption," *J. Pharm. Sci.* 77(5):390–92 (1988).

Kopecek, et al., "Polymers for colon–specific drug delivery," *J. Control. Rel.* 19:121–30 (1992).

Lehmann, et al., "Methacrylate–Galactomannan Coating for Colon–Specified Drug Delivery," *Proc. Int. Symp. Contr. Rel. Bioact. Mater.* 8:331–32 (1991).

Milojevic, et al., "In Vitro and In Vivo Evaluation of Amylose Coated Pellets for Colon Specific Drug Delivery," *Proc. Int. Symp. Contr. Rel. Bioact. Mater.* 20:288–89 (1993).

Mishima, et al., "Studies on the Promoting Effects of Medium Chain Fatty Acid Salts on the Nasal Absorption of Insulin in Rats," *J. Pharmaco–Biodynamics* 10:624–31 (1987).

Morishita, et al., "Site–Dependent Effect of Aprotitin, Sodium Caprate, $Na_2$EDTA and Sodium Glycoholate on Intestinal Absorption of Insulin," *Biol. Pharm. Bull.* 16(1):68–72 (1993).

Muranushi, et al., "Effect of Fatty Acids and Monoglycerides on Permeability of Lipid Bilayer," *Chem. Phys. Lipids* 28(3):269–79 (1981).

Muranushi, et al., "The Effects of Fatty Acids and Their Derivatives on the Intestinal Absorption of Insulin in Rat," *Drug Devel. Ind. Pharm.* 19(8):929–41 (1993).

Rubinstein, et al., "Colonic Drug Delivery: Enhanced Release of Indomethacin from Cross–Linked Chondroitin Matrix in Rat Cecal Content, " *Pharm. Res.* 9(2):276–78 (1992).

Rubinstein, et al., "In Vitro Evaluation of Calcium Pectinate: A Potential Colon–Specific Drug Delivery Carrier, " *Pharm. Res.* 10(2):258–63 (1993).

Rubinstein, et al., "Synthesis and swelling–dependent enzymatic degradation of borax–modified guar gum for colonic delivery purposes," *S.T.P. Pharma Sciences* 5:41–46 (1995).

Scott–Moncrieff, et al., "Enhancement of Intestinal Insulin Absorption by Bile Salt–Fatty Acid Mixed Micelles in Dogs," *J. Pharm. Sci.* 83(10):1465–68 (1994).

Siefke, et al., "Colon Targeting with β–CD Matrix Films," *Eur. J. Pharm. Biopharm.* 40 (suppl.):33S (1994).

Swenson, et al., "Intestinal permeability enhancement for proteins, peptides and other polar drugs mechanisms and potential toxicity," *Advan. Drug Del. Rev.* 8:39–92 (1992).

Van Den Mooter, "Azo polymers for colon–specific drug delivery," *Int. J. Pharm.* 87:37–46 (1992).

Wilding, et al., "Gastrointestinal Transit and Systemic Absorption of Captopril from a Pulsed–Release Formulation," *Pharm. Res.* 9(5):654–57 (1992).

COMPOSITION FOR ENHANCED UPTAKE OF POLAR DRUGS FROM THE COLON

Priority is claimed under 35 U.S.C. § 119 to PCT/GB96/01933, filed Aug. 8, 1996, which corresponds to GB 9516268.1, filed Aug. 8, 1995.

FIELD OF THE INVENTION

This invention relates to a drug delivery composition for colonic delivery of a polar drug, and more particularly to a composition which promotes absorption of a polar drug from the colon.

BACKGROUND

Administration of drugs to the gastrointestinal tract is a preferred method for both human and veterinary medicine. Most conventional drugs are well absorbed from the intestines, usually by a process of passive diffusion, although certain compounds are taken up by more specific mechanisms such as facilitated or active transport. Polar molecules such as cimetidine, ranitidine, sodium cromoglycate bisphosphonates (such as clodronate) and captopril often display poor or erratic absorption when dosed orally. The polypeptide and polysaccharide drugs such as insulin, calcitonin, parathyroid hormone or fractions or analogues thereof, luteinising hormone releasing hormone (LHRH) or analogues thereof (eg. nafarelin, buserelin, goserelin), growth hormone, growth hormone releasing hormones, colony stimulating factors, erythropoietin. somatostatin, interferons and heparins cannot be given orally because, not only are they poorly absorbed because of their polar nature and size, but they can also be degraded by the endogenous enzymes present in the gastrointestinal tract. If such drugs are given orally the absolute bioavailability (defined as the quantity reaching the systemic circulation) as compared to parenteral administration is generally low (less than 1%). Cyclosporin, a polypeptide, is a notable exception. It is non-polar in nature and has a partition coefficient (octanol/water) of more than 1000. This drug is quite well absorbed from the gastrointestinal tract.

Despite the inherent problems in attempting to administer polar drugs orally, various attempts have been made to improve oral absorption. Strategies have included chemical modification to stabilise the drug and/or make it more lipid soluble and hence improve its chances to diffuse across the lipid membrane or the gastrointestinal tract. Other workers have added stabilising agents such as peptidase inhibitors (eg. aprotinin) to reduce metabolic loss, while others have used various absorption promoting agents in the form of non-ionic surface active agents, bile salts and analogues thereof, phospholipids, chelating agents or acyl carnitine. These previous attempts have been well reviewed in the relevant literature.

For example the various means to enhance the intestinal permeability of proteins, peptides and other polar drugs have been reviewed by Swenson and Curatolo (Advan. Drug Del. Rev. 8, 39, 1992). While mixed systems were reported these were restricted to systems comprising bile salt/oleic acid mixtures and polyethoxylated hydrogenated castor oil/oleic acid mixtures. The ileocolonic delivery of insulin at 10 units/kg to the dog using a mixed micelle system comprising sodium glycocholate (30 mM) and a fatty acid (linoleic acid) of 40 mM has been described by Scott-Moncrieff and others, J. Pharm. Sci. 83, 1465 (1994). The reported bioavailability was 1.4%. Medium chain glycerides (MCGs) have been reported to enhance the intestinal absorption of hydrophilic drugs. For example Beskid et al. (Pharmacology, 34,. 77, 1988) reported that a formulation incorporating a mixture of glyceryl mono- and di-caprylate enhanced the absorption of an antibiotic from the intestinal tract of rats. Mixtures of medium chain glycerides with medium chain length fatty acids ($C_8$–$C_{12}$) have also been reported (see for example Muranushi et al. Chem. Phys. Lipids 28, 269, 1981).

It has been known for some time that sodium caprate can act as an absorption promoting agent, probably by the perturbation of membranes or modification of tight junctions between cells (Kajii et al. J. Pharm. Sci. 77 390, 1988). The absorption promoting effect of fatty acids has also been associated with the chelating ability for calcium ions and an inhibiting action on leucine amino peptidase activity (Mishima et al. J. Pharmaco. Biodyn. 10 624, 1987). The effect of fatty acids and their derivatives on the intestinal absorption of insulin in rat has been reported by Muranishi et al (Drug Devel. Ind. Pharm. 19 929, 1993). A critical carbon chain length ($C_{10}$) was seen with the fatty acids.

Morishita et al (Biol. Pharm. Bull. 16 68, 1993) explained different sites for the absorption of insulin from the rat intestine. They employed sodium caprate and sodium glycocholate as absorption enhancers. They concluded that the ileum was the most preferred site for insulin absorption while the colon had a greater sensitivity to the effect of the selected absorption enhancers.

The use of polyglycolysed glycerides (Labrasol) to increase the absorption of insulin has been described in European Patent No. 0351651. Formulations were prepared based on a mixture of insulin (as an aqueous solution) and LABRASOL™. Formulations were administered intraduodenally to rats (approx. 250 g) at an insulin dose of 5–20 IU/rat and a LABRASOL™ dose of 12.5–50 mg/rat. The formulations were administered to dogs as either an intraduodenal infusion or in an enteric coated capsule at approx. 12 IU/kg insulin and a high level of LABRASOL™ (80–90 mg/kg). Dogs were also administered the formulations by the buccal route at 10 IU/kg insulin and 17 mg/kg LABRASOL™.

EP 0418674 discloses antibiotic formulations based on either LABRASOL™+caprylic acid or LABRASOL™+caprylic acid+sodium caprylate. They were administered orally or rectally to animals. Orally, no drug was absorbed from the control formulation, whereas the formulations containing enhancers LABRASOL™/caprylic acid or LABRASOL™/caprylic acid/Na caprylate resulted in absorption of drug. Formulations containing the enhancers were also effective when administered rectally. The formulations were not targeted to the colon. Indeed it is well appreciated by those skilled in the art that it is inappropriate to administer antibiotics into the colonic region because of the effects on the local flora and the induction of severe clinical conditions such as pseudomembranous colitis.

WO 94/08622 describes a pharmaceutical composition containing calcitonin and a polyglycolipid glyceride to promote drug absorption that could be delivered by a variety of different routes to include mucosal surfaces. The composition was stated to have a pH of 3–5.7.

It is now appreciated that animal models may not be well predictive of man in terms of absorption from the gastrointestinal tract and moreover that cell cultures (eg. CaCo-2 confluent cell monolayers) and gut loops do not properly reflect the in vivo situation where mucus, enzymes and gastrointestinal mobility and transit can have a major influence. Davis (I. Pharm. Pharmacol. 44 Suppl. 1 186, 1992) has described these problems in detail.

Factors to be considered in the administration of polar molecules orally so as to obtain a systemic effect can be summarised as follows. The chosen materials for absorption enhancement should be approved for administration by the oral route; the chosen agent should give rise to a sufficient increase in drug absorption without apparent side effects; the final formulation should conserve the stability of the drug and be in the form of an easily administered product such as a tablet or capsule.

SUMMARY OF THE INVENTION

It has been found that polar drugs are advantageously delivered to the colon and that the absorption of polar drugs from the colon is greatly enhanced by administering the drug with a mixture of a fatty acid having 6 to 16 carbon atoms or related mono/diglycerides and a pharmaceutically acceptable dispersing agent. It has surprisingly been found that the mixture of fatty acid or related mono/diglycerides and pharmaceutically acceptable dispersing agent gives a synergistic effect which is much greater than that obtained from each agent alone.

It is therefore an object of the present invention to provide a drug delivery composition for colonic delivery comprising a polar drug an absorption promoter which (a) comprises a mixture of a fatty acid having 6 to 16 carbon atoms or a salt thereof and a dispersing agent or (b) comprises a mixture of mono/diglycerides of medium chain fatty acids and a dispersing agent and means adapted to release the polar drug and absorption promoter in the colon.

DETAILED DESCRIPTION OF THE INVENTION

The fatty acid or salt thereof, for example a sodium salt, preferably has a carbon chain of $C_6$ to $C_{14}$ and most preferably $C_8$ to $C_{10}$. A preferred fatty acid is capric acid or a salt thereof such as sodium caprate.

The term 'mono/diglycerides' is used herein to include a mixture of monoglycerides and diglycerides. Preferably the mixture contains 1% to 99% monoglycerides and 99% to 1% diglycerides; more preferably 10% to 90% monoglycerides and 90% to 10% diglycerides, and more preferably 50% to 80% monoglycerides and 50% to 20% diglycerides. The mono/diglycerides of fatty acids have fatty acids with carbon chains of $C_6$ to $C_{16}$, preferably $C_8$ to $C_{10}$. A particularly preferred material is AKOLINE™ MCM (available from Karlshamns, Sweden). Akoline is a mixture of mono-diglycerides of medium chain fatty acids. The term 'dispersing agent' is used herein to include an agent that is able to position itself at the interphase between the formulation phase and the aqueous phase in the colon and thereby reduce the interfacial tension between the two phases and promote the dispersion of the formulation in the lumen of the colon. Suitably, the dispersing agent is a pharmaceutically acceptable dispersing agent. The balance between the hydrophilic and lipophilic moieties in a surfactant molecule is used as a method of classification (hydrophile-lipophile balance, HLB). The HLB values for commonly-used surfactants are readily available in the literature (eg. Handbook of Pharmaceutical Excipients, The Pharmaceutical Press. London, 1994). The HLB system was originally devised by Griffin (J. Soc. Cosmetic Chem., 1, 311, 1949). Griffin defined the HLB value of a surfactant as the mol % of the hydrophilic groups divided by 5, where a completely hydrophilic molecule (with no non-polar groups) had an HLB value of 20. This simple approach to calculating the HLB value is only applicable to polyoxyethylene ethers. Consequently, for other surfactants, HLB values have been derived from diverse properties such as water solubility, dielectric constant, interfacial tension and cloud point. Such dispersing agents preferably have a Hydrophilic-Lipophilic-Balance (HLB number, as defined in Griffin, W C, J. Soc. Cos. Chem. 1, 1949. 311: J. Soc. Cos. Chem. 5, 1954, 249) between 1 and 20, more preferably between 3 and 19 and most preferably between 8 and 18. A pharmaceutically acceptable dispersing agent should be non-toxic and have a taste, odor and chemical stability that are compatible with the product.

Suitable dispersing agents include, but are not limited to, polyglycolyzed glycerides (eg. LABRASOL™), polyoxyethylene sorbitan fatty acid esters, e.g., polyoxyethylene 20 sorbitan monolaurate (TWEEN™ 20), polyoxyethylene (4) sorbitan monolaurate (TWEEN™ 21), polyoxyethylene 20 sorbitan monopalmitate (TWEEN™ 40), polyoxyethylene 20 sorbitan monooleate (TWEEN™ 80); polyoxyethylene alkyl ethers, e.g., polyoxyethylene 4 lauryl ether (Brij 30), polyoxyethylene 23 lauryl ether (BRIJ 35), polyoxyethylene 10 oleyl ether (BRIJ™ 97); and polyoxyethylene glycol esters, e.g., poloxyethylene 8 stearate (MYRJ™ 45), poloxyethylene 40 stearate (Myrj 52) or mixtures thereof.

The polyglycolyzed glyceride may be saturated or unsaturated and include ethoxylated glycerides and polyethylene glycol esters. A particularly preferred saturated polyglycolyzed glyceride is a glyceryl caprylate/caprate and PEG-8 (polyethylene glycol) caprylate/caprate complex known as LABRASOL™ Gattefossé Corp., New York). Suitable unsaturated polyglycolyzed glycerides are apricot kernel oil PEG-6 complex (LABRAFIL™ M-1944 CS), almond oil PEG-6 complex (LABRAFIL™ M-1966 CS), peanut oil PEG-6 complex (LABRAFIL™ M-1969 CS), olive oil PEG-6 complex (LABRAFIL™ M-1980 CS) and corn oil PEG-6 complex (LABRAFIL™ M-2125 CS), all Gattefossé Corp. New York. A suitable ethoxylated glyceride has $C_8$–$C_{10}$ carbon chain, for example glyceryl caprylate/caprate PEG-4 complex.

The ratio of the fatty acid to the dispersing agent is in the range 1:10 to 10:1, preferably 1:5 to 5:1 and most preferably 1:3 to 3:1.

The term polar is used to include compounds with a partition coefficient between water and octanol at pH 7.4 of less than 10. The polar drug preferably has a molecular weight from 100 Da to 100000 Da. The polar drug is preferably an active drug but it may be a drug in a masked form such as a prodrug. The term "active drug" is used to include compounds which are therapeutically, pharmacologically, pharmaceutically, prophylactically or diagnostically active.

The following list of polar drugs suitable for use is provided by way of illustration and is not meant to be exclusive: cimetidine, ranitidine, sodium cromoglycate and bisphosphonates such as clodronate and captopril. Polypeptide drugs such as insulin, calcitonins, parathyroid hormone or fractions thereof or analogues thereof, luteinising hormone releasing hormones or analogues thereof such as nafarelin, buserelin, goserelin, growth hormone, growth hormone releasing hormones, colony stimulating factors, erythropoietin, somatostatin and analogues such as octreotide and vapreotide, $\alpha$-,$\beta$-or $\gamma$-interferon, proinsulin, glucagon, vasopressin, desmopressin, thyroid stimulating hormone, atrial peptides, tissue plasminogen activator, factor VIII, cholecystokinin, octreotide, polysaccharide drugs such as low molecular weight heparin, genes such as DNA or DNA constructs and antisense agents.

It is preferred if the drug is not an antibacterial agent.

The composition can be formulated as a capsule formulation using hard or soft gelatine capsules or starch capsules, the polar drug being suspended in the dispersing agent-fatty acid mixture or the dispersing agent-di-triglyceride mixture or the dispersing agent-mono/diglyceride mixture.

The composition may be a liquid or semi-solid. The precise physical nature of the formulation will depend on the carbon chain length of the fatty acid included. For example, capric acid (C10) has a melting point of 32° C. A 50:50 mixture of LABRASOL™, BRIJ™ 97 or TWEEN™ 80 with capric acid will be a semi-solid at room temperature. On the other hand, caprylic acid (C8) has a melting point of 16° C. and a 50:50 mixture with LABRASOL™ will be a liquid at room temperature. Such formulations are suitable for filling into pharmaceutical capsules made of gelatin or starch or other suitable material. Technologies for liquid filling of capsules are well established. Compositions containing fatty acids with a carbon chain length >8 would be filled into the capsules as a hot melt. Liquid-filled capsules can be coated with suitable polymers in order to modify their dissolution properties. However, for hard gelatin capsules a gelatin band needs to be applied to the join between the capsule lid and body to prevent leakage of liquid contents during coating. Co-mixed or co-melted LABRASOL™/fatty acid mixtures are particularly advantageous since they form a readily dispersing mixture when the capsule into which they are filled disintegrates. Mixtures of LABRASOL™ with C6, C8 and C10 fatty acids are liquid at body temperature and will spontaneously emulsify in contact with aqueous media (eg. intestinal fluid). Mixtures of LABRASOL™ with C12, C14 and C16 fatty acids will be semi solids at body temperature and will readily disperse in contact with aqueous media.

The composition may also be formulated to contain known pharmaceutical excipients to obtain optimal pharmaceutical properties such as AVICEL™, HPMC and the like or may be formulated as a tablet or pellets (microcapsules) using known tablet constituents and methods.

In order to ensure delivery to the proximal colon a means is provided to prevent release of the polar drug and absorption promoter until the formulation reaches the colon, preferably the proximal colon. Thus, the composition comprises means adapted to release the polar drug and absorption promoter in the colon. The term 'proximal colon' is used herein to include the ascending and transverse regions.

Preferably a coating is provided on the capsule, tablet or pellet to prevent release until the tablet, capsule or pellet reaches the proximal colon. Pellets may be encapsulated in capsules.

Any coating can be used which ensures that the capsule, tablet or pellet does not break-up and release the drug until it is in the colon. The coating may be one which is pH-sensitive, redox-sensitive or sensitive to particular enzymes or bacteria, such that the coating only dissolves or finishes dissolving in the colon. Thus the capsules (or tablets or pellets) will not release the drug until it is in the colon.

The thickness of the coating will typically be in the range 80 $\mu$m to 300 $\mu$m, for example between 100 $\mu$m and 250 $\mu$m or between 150 $\mu$m and 200 $\mu$m. The thickness of the particular coating used will be chosen according to the mechanism by which the coating is dissolved.

Preferred coating materials are those which dissolve at a pH of 5 or above. The coatings therefore only begin to dissolve when they have left the stomach and entered the small intestine. A thick layer of coating is provided which will dissolve in about 3–4 hours thereby allowing the capsule underneath to breakup only when it has reached the terminal ileum or the colon. Such a coating can be made from a variety of polymers such as cellulose acetate trimellitate (CAT), hydroxypropylmethyl cellulose phthalate (HPMCP), polyvinyl acetate phthalate (PVAP), cellulose acetate phthalate (CAP) and shellac as described by Healy in his article "Enteric Coatings and Delayed Release" Chapter 7 in Drug Delivery to the Gastrointestinal Tract, editors Hardy et al., Ellis Horwood, Chichester, 1989. For coatings of cellulose esters, a thickness of 200–250 $\mu$m would be suitable.

Especially preferred materials are methylmethacrylates or copolymers of methacrylic acid and methylmethacrylate. Such materials are available as EUDRAGIT™ polymers (trademark) (Röhhm Pharma, Darmstadt, Germany). Eudragits are copolymers of methacrylic acid and methylmethacrylate. Preferred compositions are based on EUDRAGIT™ L100 and Eudragit S100. EUDRAGIT™

L100 dissolves at pH 6 and upwards and comprises 48.3% methacrylic acid units per g dry substance; EUDRAGIT™ S100 dissolves at pH 7 and upwards and comprises 29.2% methacrylic acid units per g dry substance. Preferred coating compositions are based on EUDRAGIT™ L100 and EUDRAGIT™ S100 in the range 100 parts L100:0 parts S100 to 20 parts L100:80 parts S100. The most preferable range is 70 parts L100:30 parts S100 to 80 parts L100:20 parts S100. As the pH at which the coating begins to dissolve increases, the thickness necessary to achieve colon specific delivery decreases. For formulations where the ratio of EUDRAGIT™ L100:S100 is high, a coat thickness of the order 150–200 μm is preferable. This is equivalent to 70–110 mg of coating for a size 0 capsule. For coatings where the ratio EUDRAGIT™ L100:S100 is low, a coat thickness of the order 80–120 μm is preferable, equivalent to 30 to 60 mg coating for a size 0 capsule.

The colonic region has a high presence of microbial anaerobic organisms providing reducing conditions. Thus the coating may suitably comprise a material which is redox-sensitive. Such coatings may comprise azopolymers which can for example consist of a random copolymer of styrene and hydroxyethyl methacrylate, cross-linked with divinylazobenzene synthesized by free radical polymerization, the azopolymer being broken down enzymatically and specifically in the colon, or the polymer may be a disulphide polymer (see PCT/BE91/00006 and Van den Mooter, Int. J. Pharm. 87. 37, 1992).

Other materials which provide release in the colon are amylose, for example a coating composition can be prepared by mixing amylose-butan-1ol complex (glassy amylose) with ETHOCEL™ aqueous dispersion (Milojevic et al., Proc. Int. Symp. Contr. Rel. Bioact. Mater. 20, 288, 1993), or a coating formulation comprising an inner coating of glassy amylose and an outer coating of cellulose or acrylic polymer material (Allwood et al GB 9025373.3), calcium pectinate (Rubenstein et al., Pharm. Res., 10, 258, 1993) pectin, a polysaccharide which is totally degraded by colonic bacterial enzymes (Ashford et al.; Br Pharm. Conference, 1992, Abstract 13), chondroitin sulphate (Rubenstein et al., Pharm. Res. 9. 276, 1992), resistant starches (Allwood et al., PCT WO 89/11269, 1989), dextran hydrogels (Hovgaard and Brøndsted, 3rd Eur. Symp. Control. Drug Del., Abstract Book, 1994, 87) modified guar gum such as borax modified guar gum (Rubenstein and Gliko-Kabir, S.T.P. Pharma Sciences 5, 41–46, 1995), β-cyclodextrin (Sie ke et al., Eu. J. Pharm. Biopharm. 40 (suppl), 335, 1994. saccharide containing polymers, which herein includes polymeric constructs that include a synthetic oligosaccharide-containing biopolymer including methacrylic polymers covalently coupled to oligosaccharides such as cellobiose, lactulose, raffinose, and stachyose, or saccharide-containing natural polymers including modified mucopolysaccharides such as cross-linked chondroitin sulfate and metal pectin salts, for example calcium pectate (Sintov and Rubenstein PCT/US91/03014); methacrylate-galactomannan (Lehmann and Dreher, Proc. Int. Symp. Control. Rel. Bioact. Mater. 18,. 331, 1991) and pH-sensitive hydrogels (Kopecek et al., J. Control. Rel. 19, 121, 1992). Resistant starches, e.g., glassy amylose, are starches that are not broken down by the enzymes in the tipper gastrointestinal tract but are degraded by enzymes in the colon.

Alternatively, the composition can be delivered to the colon using other known colon targeting systems. Some examples, which are not exhaustive are as follows.

The TIME CLOCK RELEASE SYSTEM™ (Pozzi et al. APV Course on Pulsatile Drug Delivery, Konigswinter, May 20, 1992) is a tablet system where a tablet core containing the active drug is coated with a layer of pharmaceutical excipients. The excipients hydrate causing the surface layer to burst at a set time. The PULSINCAP™ system is an oral pulsatile delivery system which may be configured to release its drug content at a predetermined time or place within the gastrointestinal tract. The device essentially consists of an impermeable capsule body which contains the drug, sealed at the neck orifice with a hydrogel plug. A normal gelatin cap is then placed onto the body of the device. After ingestion the gelatin cap dissolves allowing the plug to hydrate. At a predetermined and controlled time the swollen plug is ejected from the body of the device, thereby releasing the capsule contents and enabling the drug to be released. (Wilding et al., Pharm. Res. 9, 654. 1992 and Binns et al., 3rd Eur. Symp. Control. Drug Del., Abstract Book, 1994, p124).

Another system which may be used is the time controlled explosion system as in U.S. Pat. No. 4,871,549, which is incorporated herein by reference.

Delivery of polar drugs to the colon is particularly advantageous as it reduces dilution of the formulation and allows creation of locally high concentrations. This enables minimisation of the amount of formulation to be administered, which reduces adverse side-effects and also aids patient compliance.

Both fatty acids and polyglycolyzed glycerides are known individually to increase absorption of polar drugs from the colon. However, in order to achieve an acceptable effect in a large mammal such as pig or man a large quantity of the material must be used. The quantity required is too great to be administered.

It has surprisingly been found that when a mixture of fatty acid or the mono/diglycerides of fatty acids and a dispersing agent such as polyglycolyzed glyceride is used however, a synergistic increase in drug absorption is seen. This enables a much smaller volume of fatty acid and glyceride to be used so that a conventional oral dosage form such as a tablet or capsule can be used for the basis of the colon delivery system.

The results obtained with the combination are found to very similar to those that can be obtained in animal models using the bile salt material sodium deoxycholate. This material, at sufficiently high concentration, is known to act as an absorption enhancer in the gastrointestinal tract but it is associated with potential side effect (diarrhoea) and toxicity.

It will be appreciated that a method is provided for manufacturing medicaments for treating a patient for whom it is desirable to deliver to the colon of the patient a polar drug, wherein the medicament includes a composition including (a) a mixture of a fatty acid having 6 to 16 carbon atoms or a salt thereof and a dispersing agent, or (b) a mixture of mono/diglycerides of medium chain fatty acids and a dispersing agent.

Preferably, the composition for use in the manufacture of the medicament further includes means adapted to release the polar drug and absorption promoter in the colon following oral administration.

Further provided is a method of administering a polar drug to the colon of a patient, the method including administering to the patient a drug delivery composition comprising a polar drug, an absorption promoter which includes (a) a mixture of a fatty acid having 6 to 16 carbon atoms or a salt thereof and a dispersing agent, or (b) a mixture of mono/diglycerides of medium chain fatty acids and a dispersing agent and means adapted to release the polar drug and absorption promoter in the colon of the patient following oral administration.

The preferred polar drugs, fatty acids, mono/diglycerides, dispersing agents and means adapted to release the polar drug and absorption promoter for these methods of manufacturing and administration are the same as for the drug delivery compositions provided herein.

Preferred features of the drug delivery compositions and methods are described in the following examples.

EXAMPLE 1

Figure 1:
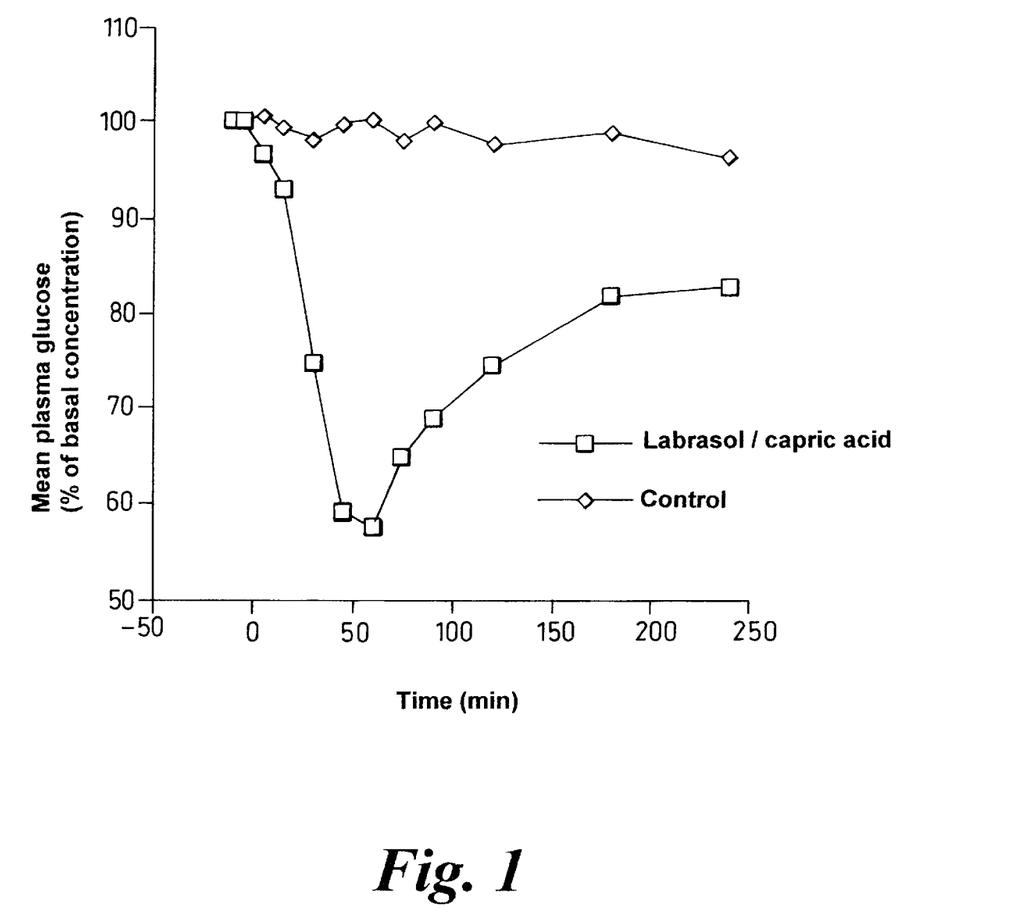
FIG. 1 is a graph showing the change in plasma glucose following administration of insulin and insulin/LABRASOL™/capric acid capsule formulations into the terminal ileum of pigs (mean data for 4 pigs).

1050 mg of LABRASOL® (Gattefossé) and 1050 mg of capric acid (Sigma) were weighed into a glass vial and warmed to 40° C. to form a homogeneous mixture. The mixture was cooled to 35° C. and 168 mg of sodium insulin (Eli Lilly; 24.7 IU/mg) added. When the insulin had evenly dispersed, 378 mg aliquots of the suspension were weighed into each of 5 size 0 starch capsules (CAPILL®, Capsugel). Each capsule contained 28 mg of insulin (692 IU), 175 mg of LABRASOL™ and 175 mg of capric acid. The capsules were administered to pigs. The pigs had been surgically modified to insert a fistula into the terminal ileum, just above the ileo-caecal valve, and cannulated at the cephalic vein to allow repeated blood sampling. Four pigs were used for the study, mean weight 31 kg. One capsule was administered to each pig, via the ileal fistula. Frequent blood samples were taken, plasma separated and analysed for glucose content. As a control, in a separate study, each pig was administered, into the ileal fistula, one starch capsule containing 28 mg of insulin and 172 mg of lactose. FIG. 1 shows the mean plasma glucose vs. time profile for the four pigs administered the insulin/LABRASOL™/capric acid formulation and the control formulation. With the control, the plasma glucose concentration remained unchanged over the duration of the study. In comparison there was a marked and prolonged fall in plasma glucose for the LABRASOL™/capric acid formulation.

EXAMPLE 2

Figure 2:
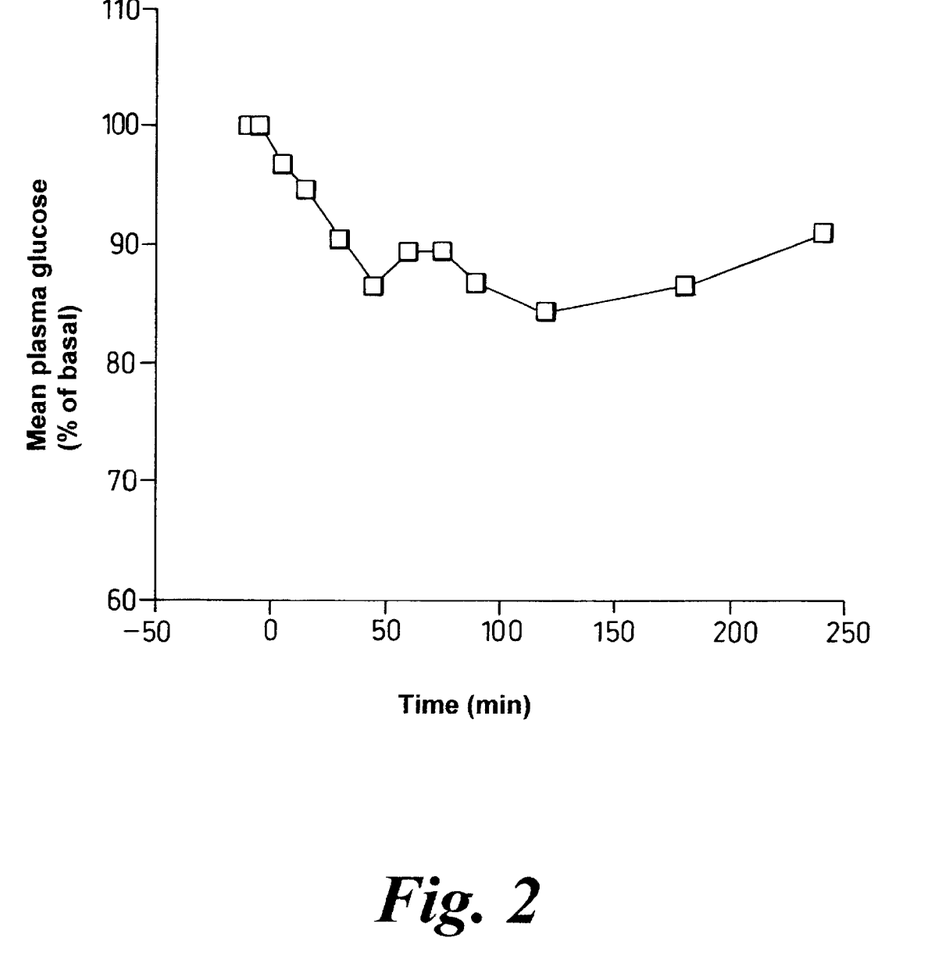
FIG. 2 is a graph showing the change in plasma glucose following administration of an insulin/LABRASOL™ capsule formulation into the terminal ileum of pigs (mean data for 3 pigs).

320 mg of sodium insulin (24.7 IU/mg) was mixed into 4000 mg of LABRASOL™. Into each of eight starch capsules was weighed 540 mg of the mixture, equivalent to 40 mg of insulin (989 IU) and 500 mg of LABRASOL™. Each of three pigs (mean weight 63 kg) was administered one of the capsules into the ileal fistula and blood samples collected for glucose analysis, as described in Example 1. The mean plasma glucose vs. time profile is shown in FIG. 2. and demonstrates that, alone, LABRASOL™ was markedly less effective as an absorption enhancer than the LABRASOL™/capric acid mixture (FIG. 1).

EXAMPLE 3

Figure 3:
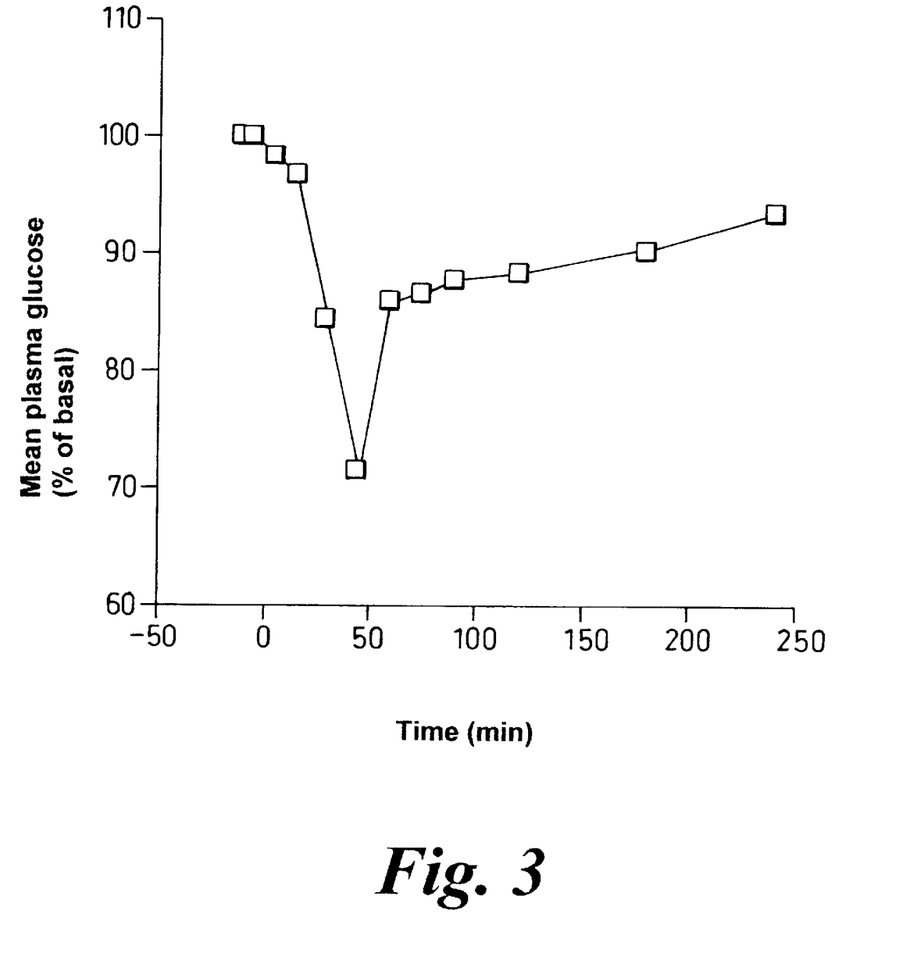
FIG. 3 is a graph showing the change in plasma glucose following administration of an insulin/capric acid capsule formulation into the terminal ileum of pigs (mean data for 3 pigs).

875 mg of capric acid was weighed into a glass vial and melted by warming to 40° C. Into the melted capric acid was stirred 202.2 mg of sodium insulin (24.7 IU/mg). Into each of four starch capsules was weighed 215.4 mg of the suspension, equivalent to 40.4 mg of insulin (1000 IU) and 175 mg of capric acid. Each of three pigs (mean weight 52 kg) was administered one of the capsules into the ileal fistula, as described in Example 1. The mean plasma glucose vs. time profile is shown in FIG. 3. Although there was a sharp drop in plasma glucose, the duration of the fall was only brief in comparison to the LABRASOL™/capric acid mixture (FIG. 1). By comparing FIGS. 1, 2 and 3, the synergistic effect of the LABRASOL™/capric acid mixture is demonstrated.

EXAMPLE 4

Figure 4:
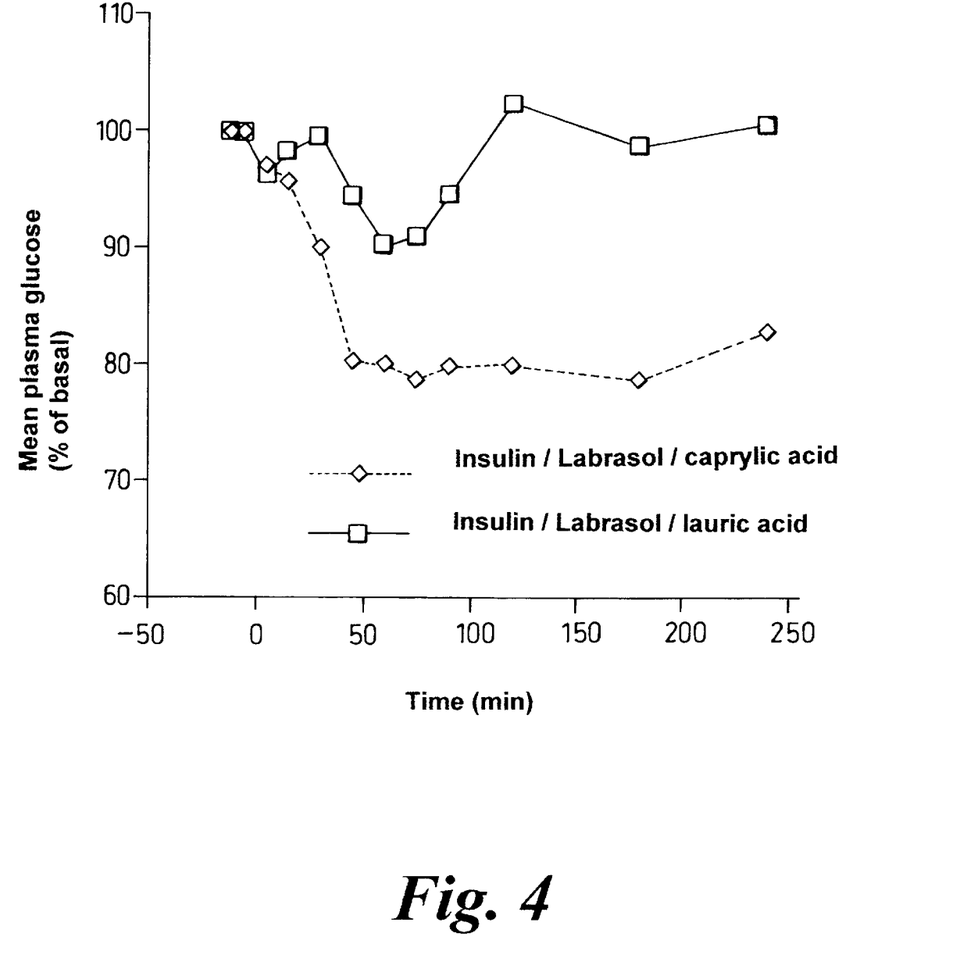
FIG. 4 is a graph showing the change in plasma glucose following the administration of insulin/LABRASOL™/caprylic acid and insulin/LABRASOL™/lauric acid capsule formulations into the terminal ileum of pigs (mean data for 4 pigs).

750 mg of caprylic acid (C8 chain length) (Sigma) and 750 mg of LABRASOL™ were weighed into a glass vial and warmed to 40° C. to form a homogenous mixture. The mixture was cooled to 35° C. and 125 mg of sodium insulin (3000 units) added. Into each of four starch capsules was weighed 325 mg of the suspension, equivalent to 150 mg capric acid, 150 mg LABRASOL™ and 600 units of insulin. Another set of capsules was prepared by weighing 750 mg of lauric acid (C12 chain length) (Sigma) and 750 mg of LABRASOL™ into a glass vial and warming to 50° C. to form a homogeneous mixture. 125 mg of sodium insulin (3000 units) was added to the melted mixture. Into each of four starch capsules was weighed 325 mg of the suspension, equivalent to 150 mg lauric acid, 150 mg LABRASOL™ and 600 units of insulin. One capsule was administered to each of four pigs (weight approx. 30 kg). with ileal fistulae as described in Example 1. Plasma samples were collected and analysed for glucose content. In FIG. 4 it can be seen LABRASOL™/caprylic acid formulation significantly enhanced insulin absorption. Although the LABRASOL™/lauric acid also lowered plasma glucose, it was less effective than the formulation containing caprylic acid.

EXAMPLE 5

Figure 5:
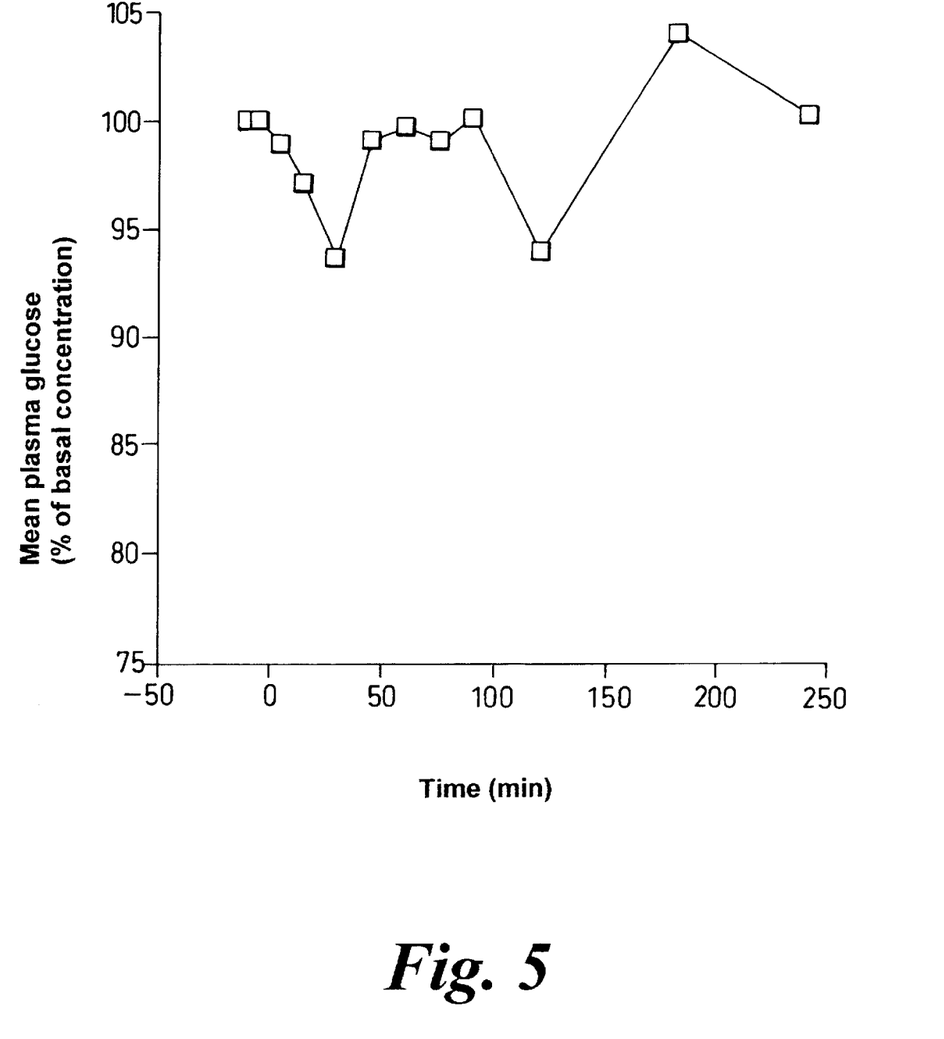
FIG. 5 is a graph showing the change in plasma glucose following administration of an insulin/LABRASOL™/stearic acid capsule formulation into the terminal ileum of pigs (mean data for 3 pigs).

875 mg of stearic acid (C18 chain length) (Sigma) and 875 mg of LABRASOL™ were weighed into a glass vial and warmed to 70° C. to form a homogeneous mixture. The mixture was cooled to 50° C. and 202.2mg of sodium insulin (5000 units) added. Into each of four starch capsules was weighed 390.4 mg of the mixture, equivalent to 175 mg stearic acid, 175 mg LABRASOL™ and 1000 units of insulin. One capsule was administered to each of four pigs (weight approx. 50 kg) with ileal fistulae as described in Example 1. Plasma samples were collected and analysed for glucose content. Plasma glucose data is shown in FIG. 5. The formulation was ineffective in lowering plasma glucose.

By comparing the data in FIGS. 1, 4 and 5, it can be seen that as the fatty acid carbon chain length is increased beyond 10, the absorption-enhancing efficacy of the formulation is reduced. This phenomenon may, in part, be related to the melting point of the fatty acid; whereas caprylic acid and capric acid will be liquids at body temperature (melting points 16° C. and 32° C. respectively), lauric and stearic acids will be semi-solid/solid (melting points 43° C. and 69° C. respectively).

EXAMPLE 6

Figure 6:
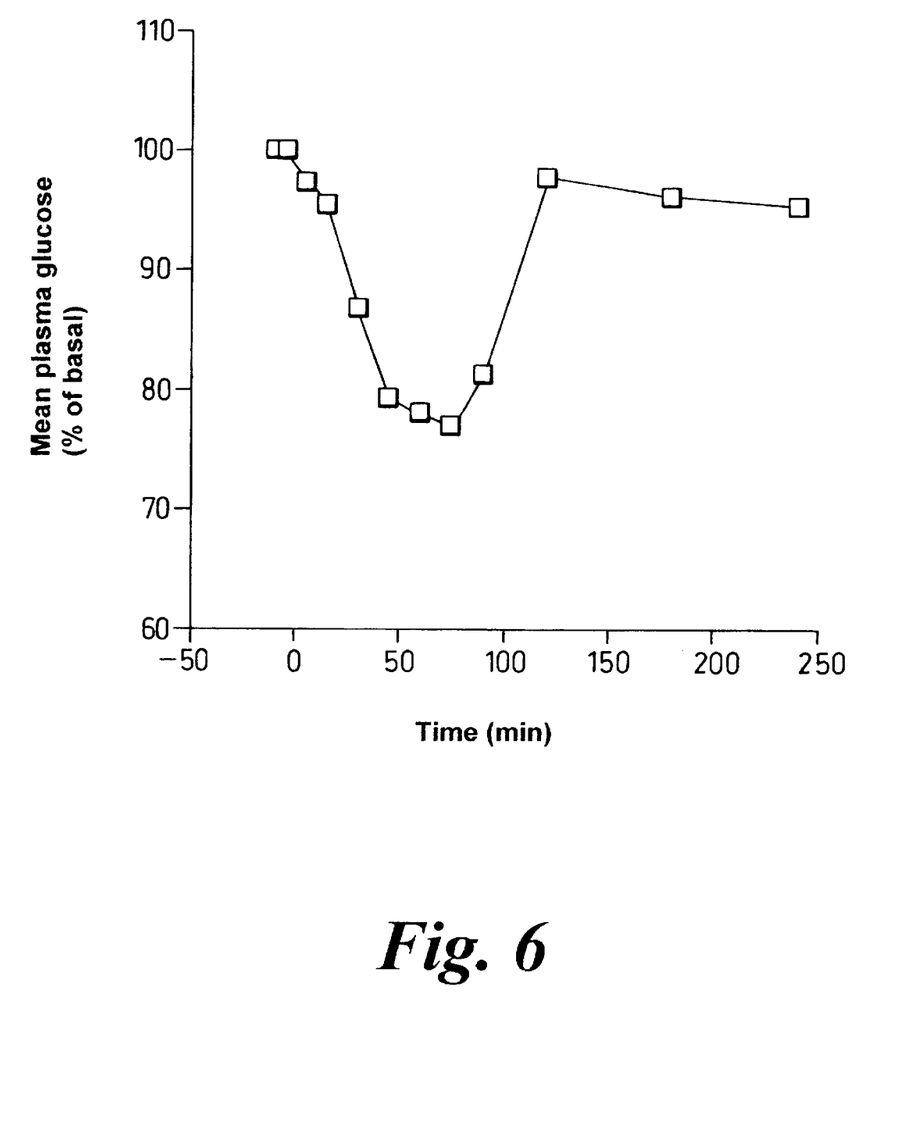
FIG. 6 is a graph showing the change in plasma glucose following administration of an insulin/capric acid/BRIJ™ 97 capsule formulation into the terminal ileum of pigs (mean data for 4 pigs).

875 mg of capric acid and 875 mg of polyoxyethylene 10 oleyl ether (BRIJ® 97,ICI) were weighed into a glass vial and warmed to 40° C. to form a homogeneous mixture. The mixture was cooled to 35° C. and 145.9 mg of sodium insulin (3500 units) added. Into each of four starch capsules was weighed 379.2 mg of the suspension, equivalent to 175 mg capric acid, 175 mg Brij 97 and 700 units insulin. One capsule was administered to each of four pigs (weight approx. 35 kg) with ileal fistulae as described in Example 1. Plasma samples were collected and analysed for glucose content. FIG. 6 shows the plasma glucose/time curve for the formulation. A pronounced and prolonged fall in plasma glucose was produced.

EXAMPLE 7

Figure 7:
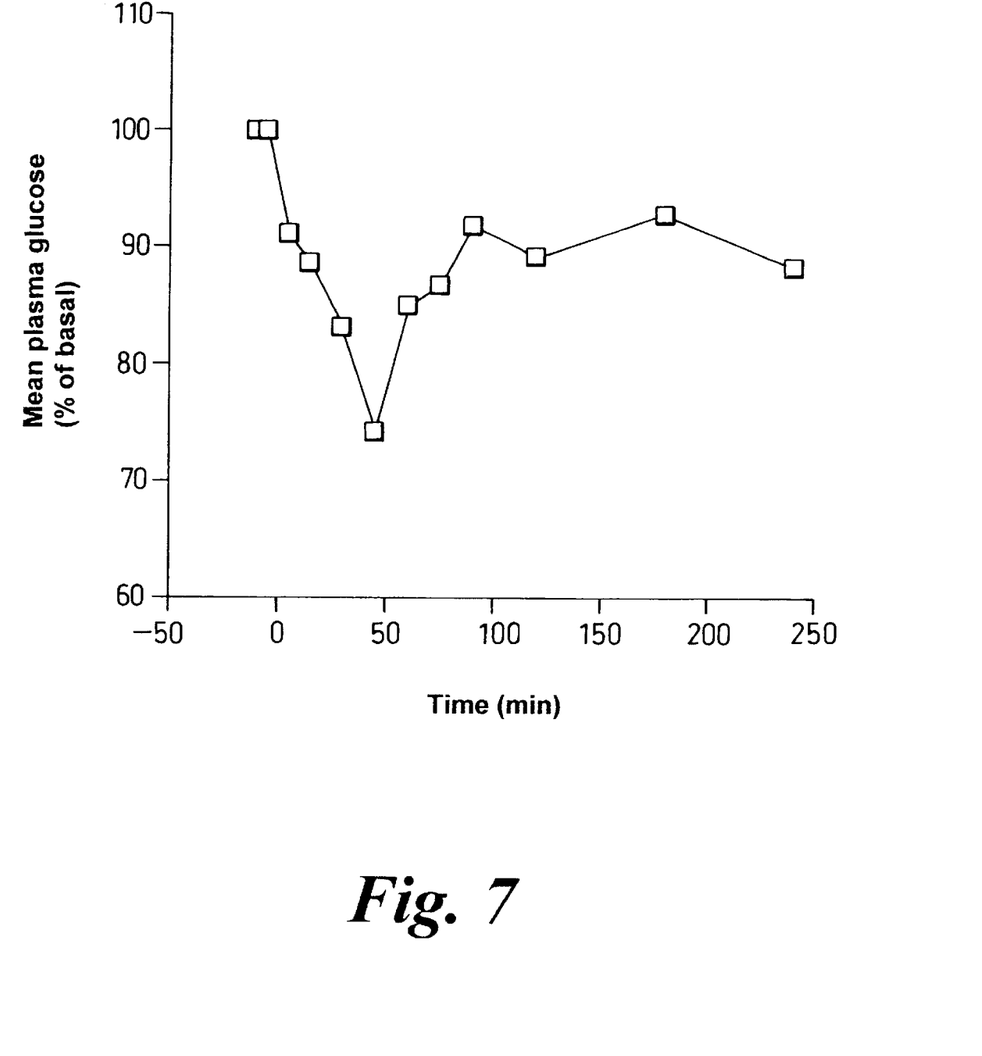
FIG. 7 is a graph showing the change in plasma glucose following administration of an insulin/capric acid/TWEEN™ 80 formulation into the terminal ileum of pigs (mean data for 4 pigs).

750 mg of capric acid and 750 mg of polyoxyethylene sorbitan monooleate (TWEEN 80, ICI) were weighed into a glass vial and warmed to 40° C. to form a homogeneous mixture. The mixture was cooled to 35° C. and 125 mg of sodium insulin (3000 units) added. Into each of four starch capsules was weighed 325 mg of the suspension, equivalent to 150 mg capric acid, 150 mg TWEEN™80 and 600 units insulin. One capsule was administered to each of four pigs (weight approx. 30 kg) with ileal fistulae as described in Example 1. Plasma samples were collected and analysed for glucose content. FIG. 7 shows the plasma glucose/time curve for the formulation. A sharp fall in plasma glucose of relatively short duration was produced.

EXAMPLE 8

Figure 8:
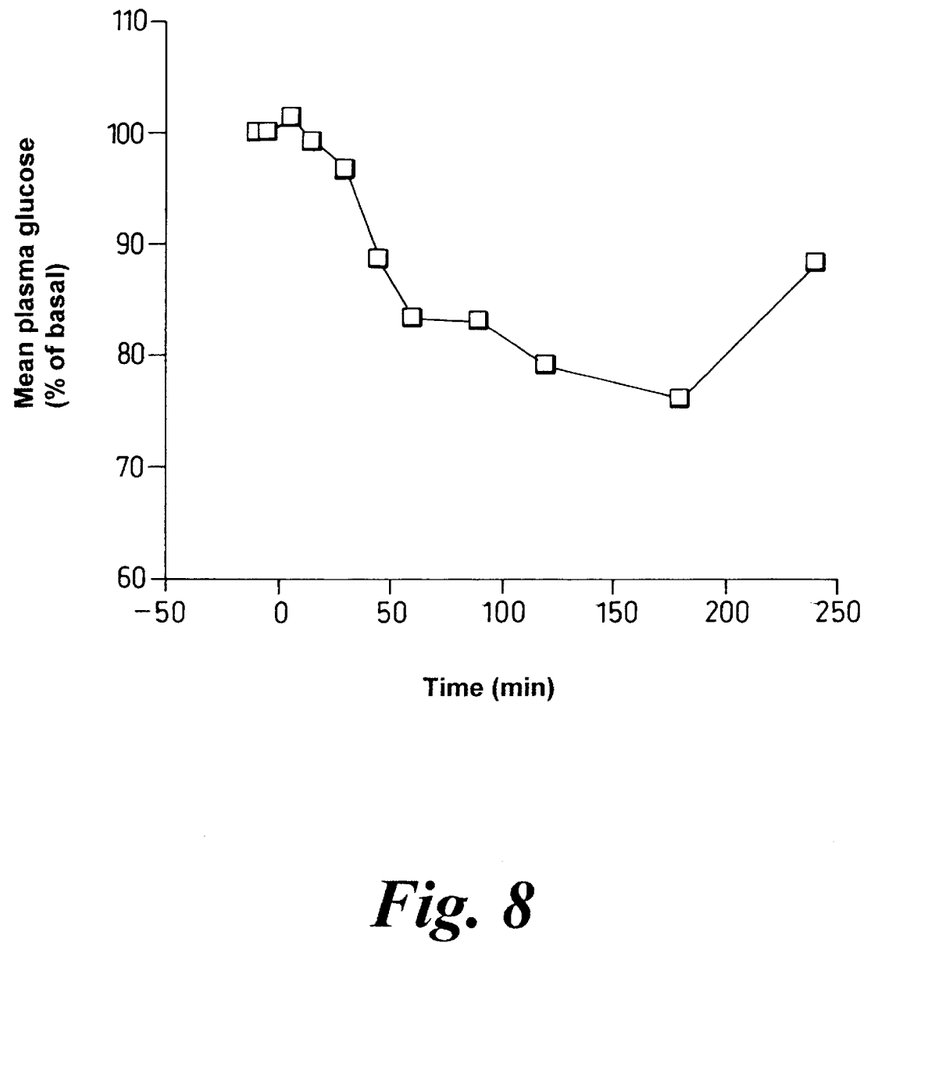
FIG. 8 is a graph showing the change in plasma glucose following administration of an insulin/LABRASOL™/capric acid/AVICEL™ capsule formulation into the terminal ileum of pigs (mean data for 4 pigs).

600 mg of LABRASOL™ and 300 mg of capric acid were weighed into a glass vial and warmed to 40° C. to form a homogenous mixture. To the LABRASOL™/capric acid was added 900 mg of microcrystalline cellulose (AVICEL™ PH 102, FMC) followed by 325 mg of sodium insulin (7200 units). Into each of four starch capsules was weighed 354 mg of the paste, equivalent to 100 mg LABRASOL™, 50 mg capric acid and 1200 units of insulin. Hence, each capsule contained a smaller quantity of absorption enhancers compared to Example 1; a LABRASOL™/capric acid ratio of 2:1 (previously 1:1). One capsule was administered to each of four pigs (weight approx. 60 kg) with ileal fistulae as described in Example 1. Plasma samples were collected and analysed for glucose content. FIG. 8 shows the plasma glucose/time curve for the formulation. The formulation was still effective in lowering plasma glucose despite the reduced quantities of LABRASOL™ and capric acid.

EXAMPLE 9

Figure 9:
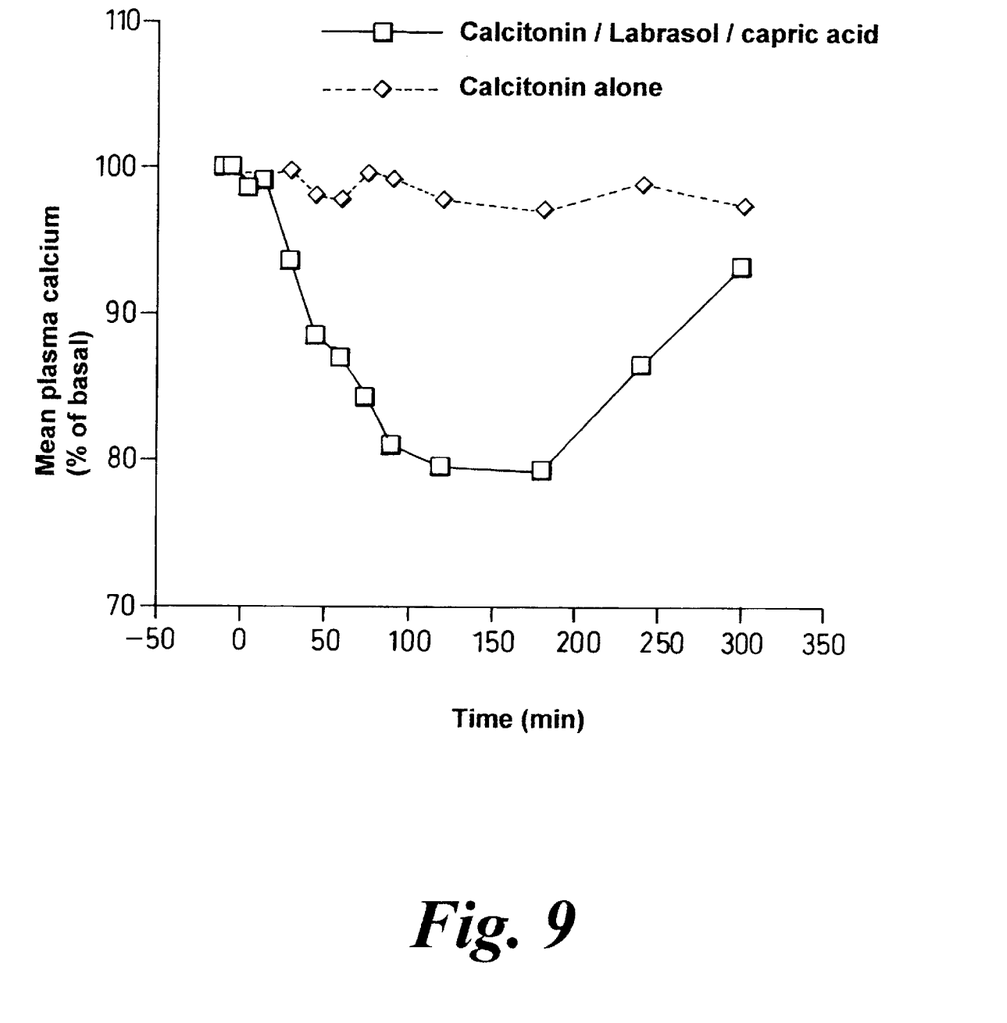
FIG. 9 is a graph showing the change in plasma calcium following administration of calcitonin and calcitonin/LABRASOL™/capric acid capsule formulations into the terminal ileum of pigs (mean data for 4 pigs).

Granules were prepared comprising salmon calcitonin, mannitol and buffer salts. Into a glass vial were weighted 1200 mg of LABRASOL™ and 400 mg of capric acid. The vial contents were heated to 40° C. and mixed until the capric acid had dispersed. Into the LABRASOL™/capric acid mixture was mixed 1200 mg of the salmon calcitonin granules (=60000 IU salmon calcitonin). Into each of four starch capsules was weighed 350 mg of the mixture, equivalent to 150 mg LABRASOL™. 50 mg capric acid and 150 mg calcitonin granules (7500 IU calcitonin) a LABRASOL™/capric acid ratio of 3:1. One capsule was administered to each of four pigs (approx. weight 100 kg) through the ileal fistula as described in Example 1. Blood samples were collected at frequent intervals and the plasma fraction separated and assayed for calcium content. The mean plasma calcium vs. time curve for the formulation is shown in FIG. 9. In a separate experiment, each of four pigs weighing 50 kg was administered a single capsule containing 22500 IU of calcitonin and 196 mg of lactose. The mean plasma calcium vs. time curve for tile formulation is also shown in FIG. 9. The control formulation resulted in a negligible fall in plasma calcium despite the dose being three times higher than the enhancer formulation and the pigs weighing 50 kg less. This further emphasised the effectiveness of the LABRASOL™/capric acid formulation.

EXAMPLE 10

Figure 10:
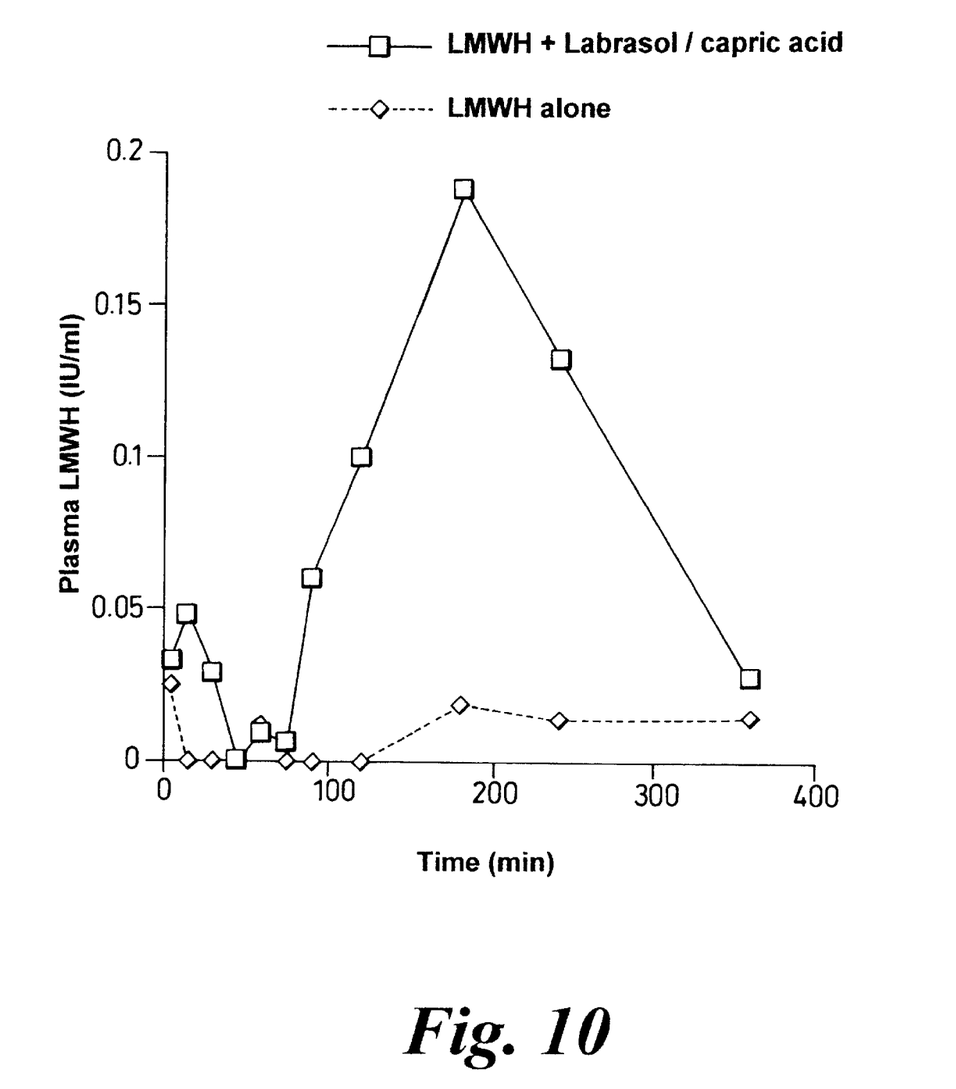
FIG. 10 is a graph showing the absorpution of low molecular weight heparin (LMWH) from capsule formulations administered into the terminal ileum of the pig and containing LMWH alone or LMWH/LABRASOL™/capric acid (mean data for 4 pigs).

Into a glass vial was weighed 875 mg of LABRASOL™ and 875 mg of capric acid. The vial contents were heated to 40° C. until the capric acid has dispersed. 1741 mg of low molecular weight heparin (LMWH. 145 IU/mg) was added to the melted LABRASOL™/capric acid mixture. Into each of eight starch capsules was weighed 349 mg of the mixture, equivalent to 174 mg of LMWH, 87.5 mg LABRASOL™ and 87.5 mg capric acid. Each of four pigs weighing approximately 65 kg was administered two of the capsules into the ileal fistula as described in Example 1. As controls, each pig was administered two starch capsules containing 174 mg of LMWH powder. Plasma samples were collected and the anti-factor Xa activity measured using a proprietary assay kit. By measuring the anti-factor Xa activity in standards containing known quantities of LMWH. tile LMWH content of the pig plasma samples was calculated. The plasma LMWH concentration vs. time profiles for the enhancer and control formulations are shown in FIG. 10. The formulation containing LABRASOL™ and capric acid was effective in enhancing colonic absorption of LMWH.

EXAMPLE 11

Figure 11:
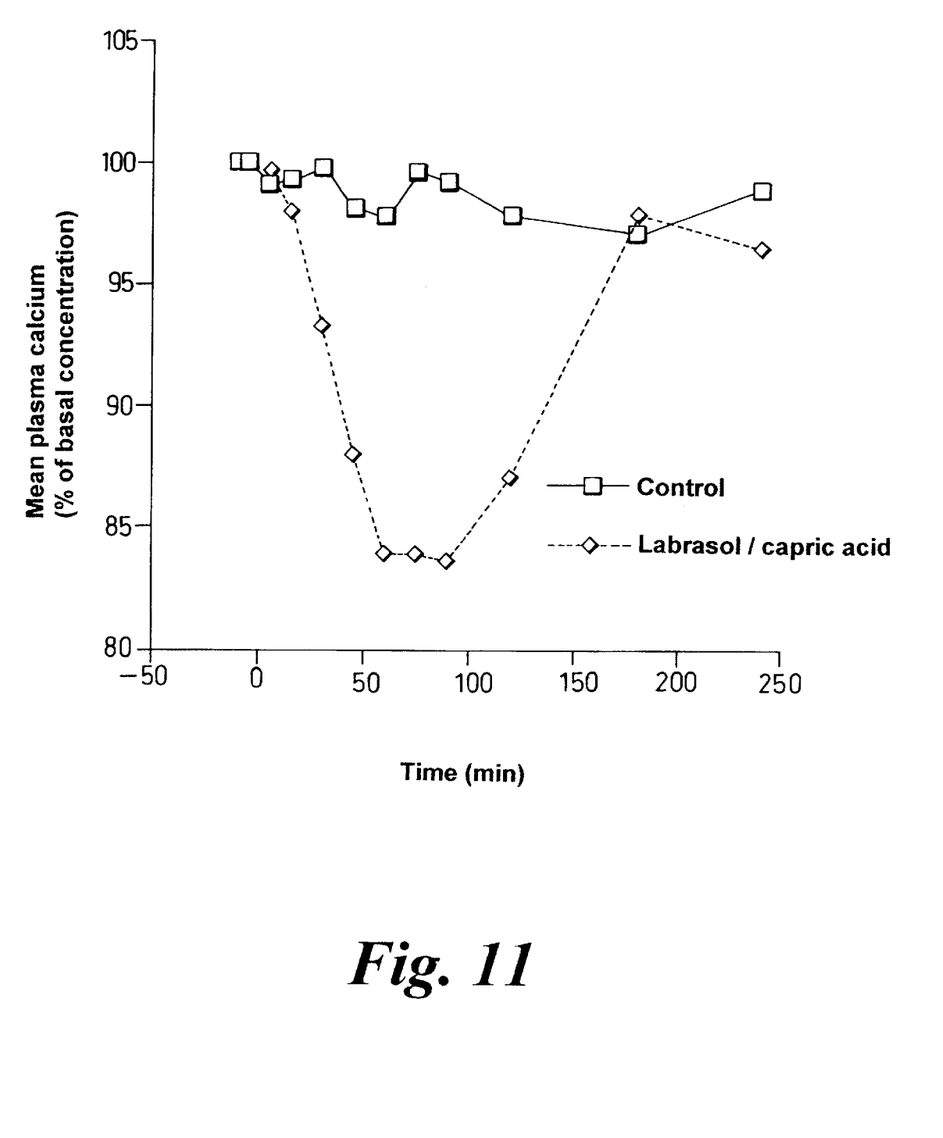
FIG. 11 is a graph showing the change in plasma calcium following administration of calcitonin and calcitonin/LABRASOL™/capric acid capsule formulations into the terminal ileum of pigs (mean data for 4 pigs).

Into a glass vial were weighed 1050 mg of LABRASOL™ and 1050 mg of capric acid: The vial contents were heated to 40° C. and mixed until the capric acid had dispersed. Into the LABRASOL™/capric acid mixture was mixed 24.55 mg of the salmon calcitonin (Carlbiotech, Copenhagen; 5500 IU/mg) When the salmon calcitonin had evenly dispersed, 354 mg aliquots of the suspension were weighed into each of five starch capsules. A capsule containing 4.09 mg of salmon calcitonin, 175 mg LABRASOL™ and 175 mg capric acid was administered to each of four pigs (approx. weight 47 kg) through the ileal fistula as described in Example 1. Blood samples were collected at frequent intervals and the plasma fraction separated and assayed for calcium content. The mean plasma calcium vs. time curve for the formulation is shown in FIG. 11. As a control, each of the four pigs was administered a single capsule containing 4.1 mg of calcitonin and 196 mg of lactose. The mean plasma calcium vs. time curve for the formulation is also shown in FIG. 11. The control formulation resulted in a negligible fall in plasma calcium whereas for the formulation containing LABRASOL™ and capric acid there was a prolonged and deep drop in plasma calcium.

EXAMPLE 12

Into a glass vial were weighed 875 mg of LABRASOL™ and 875 mg of capric acid. The vial contents were heated to 40° C. and mixed until the capric acid had dispersed. Into the LABRASOL™/capric acid mixture was stirred 60 mg of captopril (Sigma). When the captopril had evenly dispersed, 470 mg aliquots of the suspension were weighed into each of 4 size 0 starch capsules. Each capsule contained 120 mg of captopril, 175 mpg of LABRASOL™ and 175 mg of capric acid.

What is claimed is:

1. A drug deliver composition for colonic delivery comprising
   (a) a polar drug;
   (b) an absorption promoter comprising a mixture of
      (i) a dispersing agent, and
      (ii) a substance selected from the group consisting of fatty acids having 6 to 16 carbon atoms, salts of fatty acids having 6 to 16 carbon atoms, and mono/diglycerides of fatty acids having fatty acids with carbon chains of 6 to 16 carbon atoms; and
   (c) a means provided to prevent release of the polar drug and absorption promoter until the composition reaches the terminal ileum or the colon following oral administration,
   wherein the means is a formulation selected from the group consisting of capsules, tablets, and pellets, coated with a material having a thickness between about 80 μm and 300 μm which is dissolved by the conditions found in the intestines.

2. The drug delivery composition of claim 1 wherein the ratio of fatty acid to dispersing agent is in the range of between about 1:10 and 10:1.

3. The drug delivery composition of claim 1 wherein the fatty acid is capric acid or a salt thereof.

4. The drug delivery composition of claim 1 wherein the dispersing agent is selected from the group consisting of polyglycolysed glycerides, polyoxyethylene sorbitan fatty acid esters, polyoxyethylene alkyl ethers, polyoxyethylene glycol esters, and mixtures thereof.

5. The drug delivery composition of claim 4 wherein the polyglycolysed glyceride is a glyceryl caprylate/caprate and PEG-8 caprylate/caprate complex.

6. The drug delivery composition of claim 1 wherein the polar drug is selected from the group consisting of insulin, calcitonin, desmopressin, hormones, growth hormone releasing hormones, colony stimulating factors, parathyroid hormone, luteinising hormone releasing hormones, interferons, erythropoietin, bisphosphonates, antisense agents, and DNA.

7. The drug delivery composition of claim 1 wherein the polar drug and absorption promoter are released in the proximal colon following oral administration.

8. The drug delivery composition of claim 1 wherein the coating comprises a material which is redox-sensitive.

9. The drug delivery composition of claim 8 wherein the coating comprises an azopolymer or a disulphide polymer.

10. The drug delivery composition of claim 1 wherein the coating comprises a material which is degraded by enzymes or bacteria present in the colon.

11. The drug delivery composition of claim 1 wherein the coating comprises a material which dissolves at a pH of 5 or above.

12. The drug delivery composition of claim 11 wherein the coating comprises methylmethacrylate or a copolymer of methacrylic acid and methyl methacrylate.

13. The drug delivery composition of claim 11 wherein the coating comprises a cellulose ester.

14. A method for enhancing delivery of a polar drug to the colon comprising incorporating the polar drug in an absorption promoter comprising a mixture of
   (a) a dispersing agent, and
   (b) a substance selected from the group consisting of fatty acids halving 6 to 16 carbon atoms, salts of fatty acids having 6 to 16 carbon atoms, and mono/diglycerides of medium chain fatty acids, providing a means to prevent release of the polar drug and absorption promoter until the drug and absorption promoter reach the terminal ileum or the colon following oral administration wherein the means is a formulation selected from the group consisting of capsules, tablets, and pellets, coated with a material having a thickness between about 80 μm and 300 μm which is dissolved by the conditions found in the intestines.

15. A method of administering a polar drug to the colon of a patient in need thereof comprising administering to the patient a drug delivery composition comprising
   (a) a polar drug;
   (b) an absorption promoter comprising a mixture of
      (i) a dispersing agent, and
      (ii) a substance selected from the group consisting of fatty acids having 6 to 16 carbon atoms, salts of fatty acids having 6 to 16 carbon atoms, and mono/diglycerides of medium chain fatty acids; and
   (c) a means provided to prevent release of the polar drug and absorption promoter until the composition reaches the terminal ileum or the colon following oral administration.
   wherein the means is a formulation selected from the group consisting of capsules, tablets, and pellets, coated with a material having a thickness between about 80 μm and 300 μm which is dissolved by the conditions found in the intestines.

16. The drug delivery composition of claim 1 wherein the composition is formulated into pellets encapsulated in a capsule coated with the material which is dissolved by the conditions found in the intestines.

* * * * *